(12) United States Patent
Kankan et al.

(10) Patent No.: US 8,183,269 B2
(45) Date of Patent: May 22, 2012

(54) PROCESS FOR THE PREPARATION OF RUFINAMIDE

(75) Inventors: Rajendra Narayanrao Kankan, Maharashtra (IN); Dharmaraj Ramachandra Rao, Maharashtra (IN); Dilip Ramdas Birari, Maharashtra (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 13/063,440

(22) PCT Filed: Oct. 9, 2009

(86) PCT No.: PCT/GB2009/002419
§ 371 (c)(1),
(2), (4) Date: May 5, 2011

(87) PCT Pub. No.: WO2010/043849
PCT Pub. Date: Apr. 22, 2010

(65) Prior Publication Data
US 2011/0207938 A1    Aug. 25, 2011

(30) Foreign Application Priority Data
Oct. 13, 2008 (IN) .......................... 2190/MUM/2008

(51) Int. Cl.
*A61K 31/41* (2006.01)
*C07D 249/00* (2006.01)
(52) U.S. Cl. ........................ 514/359; 548/255
(58) Field of Classification Search ........... 514/359; 548/255
See application file for complete search history.

(56) References Cited

U.S. PATENT DOCUMENTS
4,789,680 A * 12/1988 Meier ............................ 514/359

FOREIGN PATENT DOCUMENTS
WO    9802423 A1    1/1998
WO    9856772 A1    12/1998
WO    2010043849 A1    4/2010

OTHER PUBLICATIONS

Foreign communication from the priority application—International Search Report and Written Opinion, PCT/GB2009/002419, 9 pages, Mar. 24, 2010.
Sultan T. Abu-Orabi, et al., "Effect of Solvent and Reaction Time on the Products of the 1,3-Dipolar Cycloaddition of Substituted Benzyl Azides with Di-tert-butyl Acetylenedicarboxylate," Gazzetta Chimica Italiana, vol. 122, pp. 29-33, 1992, XP008120316, Societa Chimica Italiana.
Foreign communication from the priority application—International Preliminary Report on Patentability, PCT/GB2009/002419, 10 pages, Apr. 19, 2011.
Wang, J., et al., Synthesis and anticonvulsant activity of 1-substituted benzyl-N-substituted-1, 2, 3-triazole-4-formamides, Progress in Natural Science, Sep. 2006, pp. 925-929, vol. 16, No. 9.
Foreign communication from a related counterpart application—EP Application Serial No. 09744712.2, Feb. 3, 2012, 8 pages.

* cited by examiner

*Primary Examiner* — Susannah Chung
(74) *Attorney, Agent, or Firm* — Conley Rose, P.C.; Rodney B. Carroll

(57) ABSTRACT

The present invention relates to a process for the preparation of rufinamide of formula I, which process comprises: (i) reacting a 2,6-difluorobenzylhalide of formula II, wherein X is chloride, bromide or iodide, with an azide to obtain 2-(azidomethyl)-1,3-difluorobenzene of formula III; (ii) reacting 2-(azidomethyl)-1,3-difluorobenzene of formula III with methyl propiolate to obtain methyl 1-(2,6-difluorobenzyl)-1H-1,2,3-triazole-4-carboxylate of formula IV; and (iii) reacting methyl 1-(2,6-difluorobenzyl)-1H-1,2,3-triazole-4-carboxylate of formula IV with ammonia to obtain rufinamide of formula I.

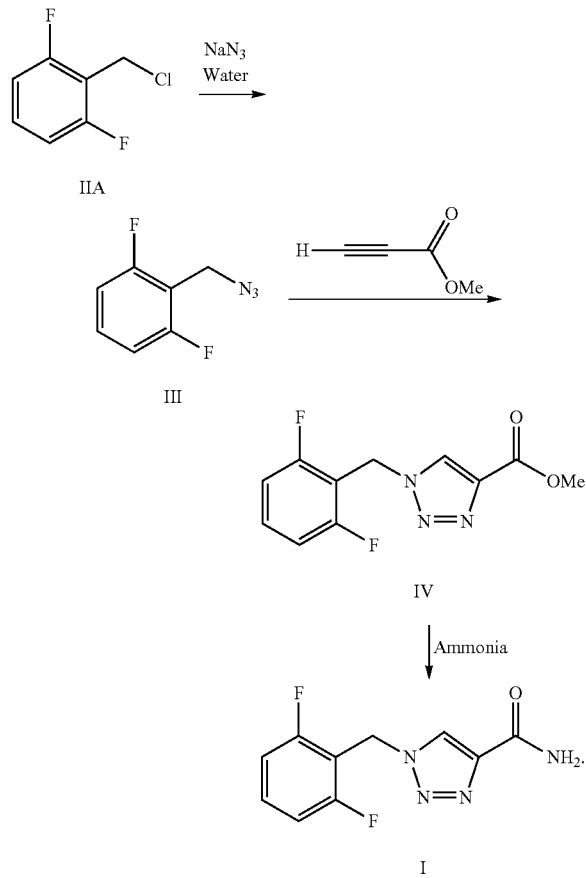

12 Claims, No Drawings

PROCESS FOR THE PREPARATION OF RUFINAMIDE

CROSS-REFERENCE TO RELATED APPLICATIONS

This application is a filing under 35 U.S.C. 371 of International Application No. PCT/GB2009/002419 filed Oct. 13, 2009, entitled "Process for the Preparation of Rufinamide," claiming priority of Indian Patent Application No. 2190/MUM/2008 filed Oct. 13, 2008, which applications are incorporated by reference herein in their entirety.

FIELD OF INVENTION

The present invention relates to an improved process for the preparation of rufinamide.

BACKGROUND OF THE INVENTION

Rufinamide is an anticonvulsant medication. It has been used in combination with other medication and therapy to treat Lennox-Gastaut spasms and various other seizure disorders. Rufinamide, a triazole derivative, was developed in 2004 by Novartis Pharma, AG, and is manufactured by Eisai. The chemical name for rufinamide is 1-(2,6-difluorobenzyl)-1H-1,2,3-triazole-4-carboxamide (formula I), and it is represented by the following structure.

Rufinamide was first described in U.S. Pat. No. 4,789,680. The synthetic method employed is depicted in the following reaction Scheme 1.

2,6-difluorobenzylchloride of formula II and sodium azide are reacted in the presence of DMSO to obtain 2-(azidomethyl)-1,3-difluorobenzene of formula III, which is then treated with 2-propiolic acid to give a carboxylic acid intermediate which on further reaction with methanol in the presence of sulfuric acid yields methyl 1-(2,6-difluorobenzyl)-1H-1,2,3-triazole-4-carboxylate intermediate of formula IV. This intermediate is then isolated and further reacted with methanolic ammonia to yield rufinamide of formula I.

U.S. Pat. No. 4,789,680 also discloses the preparation of rufinamide by reacting 2,6-difluorobenzyl azide of formula III with propiolic acid to give the corresponding carboxylic acid intermediate which is then treated with thionyl chloride and subsequently with ammonia to obtain rufinamide.

WO 1998/002423 discloses a process for preparation of rufinamide which involves reacting 2,6-difluorobenzylazide with 2-chloroacrylonitrile.

The synthesis of rufinamide described in the earlier processes involves the isolation of intermediates at each step, and then subjection of the isolated intermediates to new reagents which require different conditions, solvents, temperature, etc. Due to the multistep extractive workup procedures, there is an increase in the processing time period along with an increase in the usage of solvent. Such discontinuous processes lead to lower yield, as product is lost during each isolation step and increases the effluent load. Further, the synthesis described in the prior art involves the use of environmentally unfriendly organic solvents. It is therefore evident that there is a need for an alternative process for synthesizing rufinamide which avoids multiple isolation steps, the use of multiple reaction vessels and the use of organic solvent, and which results in a high yield.

OBJECTS OF THE INVENTION

The object of the present invention is to provide an improved process for the preparation of rufinamide.

Another object of the invention is to provide a process for the preparation of rufinamide which is simple, economical, and eco-friendly with reduced reaction times.

SUMMARY OF THE INVENTION

According to a first aspect of the present invention, there is provided a process for the preparation of rufinamide of formula I

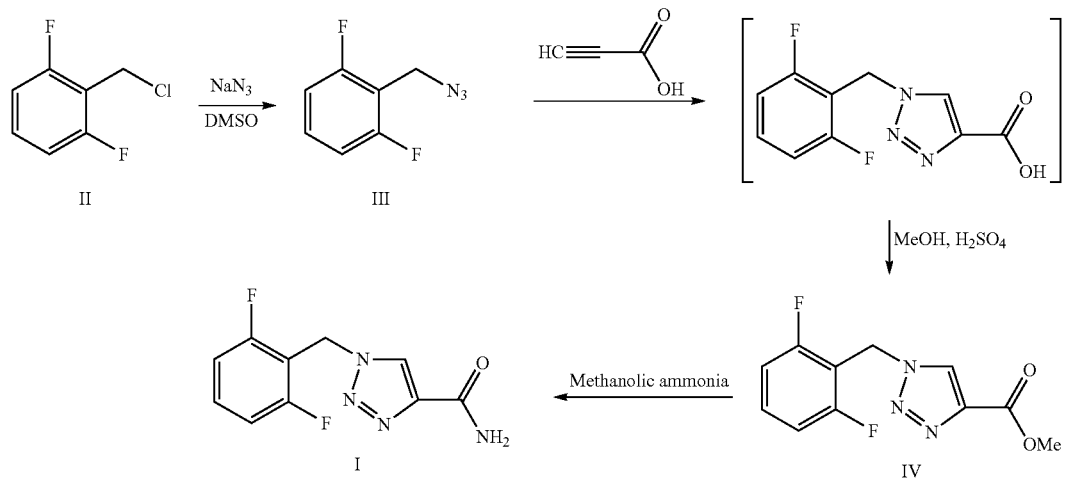

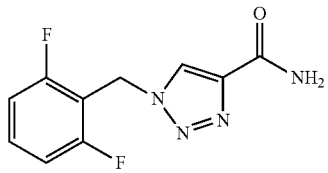

I which process comprises: (i) reacting a 2,6-difluorobenzyl-halide of formula II, wherein X is chloride, bromide, or iodide, with an azide to obtain 2-(azidomethyl)-1,3-difluorobenzene of formula III;

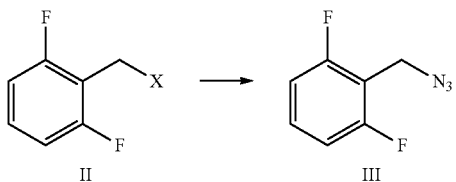

(ii) reacting 2-(azidomethyl)-1,3-difluorobenzene of formula III with methyl propiolate to obtain methyl 1-(2,6-difluorobenzyl)-1H-1,2,3-triazole-4-carboxylate of formula IV; and

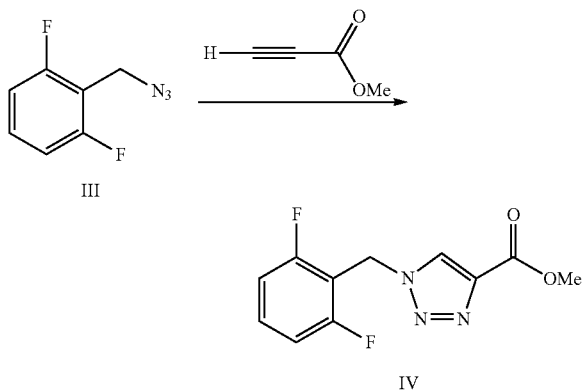

(iii) reacting methyl 1-(2,6-difluorobenzyl)-1H-1,2,3-triazole-4-carboxylate of formula IV with ammonia to obtain rufinamide of formula I.

In an embodiment, X is chloride and the compound of formula II has the formula IIA.

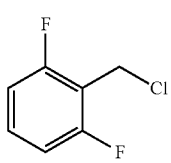

In an embodiment, X is bromide and the compound of formula II has the formula IIB.

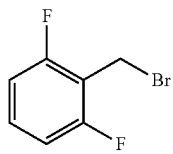

In an embodiment, the azide is an alkali metal azide, an alkyl silyl azide or a phosphoryl azide. The alkali metal azide may be sodium azide or potassium azide. Preferably, the alkali metal azide is sodium azide. The alkyl silyl azide may have the formula $R_3Si-N_3$, wherein each R is a $C_1$ to $C_6$ alkyl group, for example, methyl, ethyl, n-propyl, i-propyl, butyl, pentyl, or hexyl. Preferably, the alkyl silyl azide is trimethylsilyl azide. Alternatively, the azide is a phosphoryl azide, for example having the formula $P(O)(OR')_2N_3$, wherein each R' is a $C_1$ to $C_6$ alkyl group or optionally substituted aryl. Suitably, R' is unsubstituted phenyl.

The ammonia used in step (iii) may be in the form of gaseous ammonia, liquid ammonia, or aqueous ammonia, preferably aqueous ammonia. Suitably, the concentration of the aqueous ammonia ranges from about 20% to about 25%. Typically, the aqueous ammonia is added dropwise.

In an embodiment, step (i) is carried out at a temperature ranging from about 60° C. to about 80° C., preferably ranging from about 70° C. to about 75° C.

In an embodiment, the reaction time for step (i) ranges from about 25 hours to about 40 hours, and preferably from about 25 hours to about 30 hours.

In another embodiment, in step (ii), the methyl propiolate is added to the 2-(azidomethyl)-1,3-difluorobenzene intermediate of formula III dropwise at a temperature ranging from about 20° C. to about 30° C. (suitably about 25° C.). Then, the temperature may be raised to a temperature ranging from about 50° C. to about 75° C., preferably to a temperature ranging from about 60° C. to about 65° C., and the time required for the step (ii) ranges from about 4 to about 5 hours.

In an embodiment, all the reaction steps are carried out in the presence of water as a solvent. By this, it is meant that water is the only solvent.

Suitably, steps (i) to (iii) are carried out without isolation of 2-(azidomethyl)-1,3-difluorobenzene of formula III and without isolation of methyl 1-(2,6-difluorobenzyl)-1H-1,2,3-triazole-4-carboxylate of formula IV. In other words, neither one of these intermediates is isolated from the reaction mixture as a solid.

In an embodiment, the process is a one-pot process. In other words, all the steps that result in rufinamide in the process of the present invention are carried out in a single reaction vessel.

According to another aspect of the present invention, there is provided rufinamide prepared according to the process of the present invention.

According to another aspect of the present invention, there is provided a pharmaceutical composition comprising rufinamide prepared according to the process of the present invention together with one or more pharmaceutically acceptable excipients.

According to another aspect of the present invention, there is provided rufinamide prepared according to the process of the present invention for use in treating epilepsy or subindications thereof.

According to another aspect of the present invention, there is provided a method of treating epilepsy or a subindication thereof, the method comprising administering to a subject in need thereof a therapeutically effective amount of rufinamide prepared according to the process of the present invention.

Thus, the present invention is advantageous as it provides an improved process for preparing rufinamide which process involves the use of methyl propiolate. The use of methyl propiolate, rather than propiolic acid, as in the prior art, reduces the reaction times and allows the use of water as the solvent, which is environmentally friendly and safe. According to another aspect of the present invention, there is provided the use of methyl propiolate in a process for preparing rufinamide. In an embodiment, the process is carried out in water as a solvent. Suitably, the process is a one-pot process.

The process may involve reacting 2-(azidomethyl)-1,3-difluorobenzene of formula III with methyl propiolate, to obtain methyl 1-(2,6-difluorobenzyl)-1H-1,2,3-triazole-4-carboxylate of formula IV, and converting the methyl 1-(2,6-difluorobenzyl)-1H-1,2,3-triazole-4-carboxylate of formula IV to rufinamide.

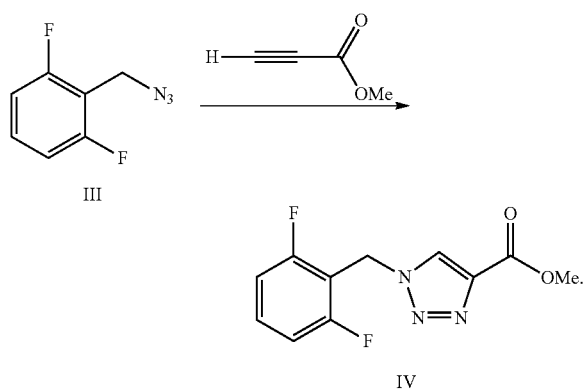

The same reaction conditions as described above in relation to the first aspect of the invention may be applied to this step.

The conversion of methyl 1-(2,6-difluorobenzyl)-1H-1,2,3-triazole-4-carboxylate of formula IV to rufinamide may comprise reacting the methyl 1-(2,6-difluorobenzyl)-1H-1,2,3-triazole-4-carboxylate of formula IV with ammonia to obtain rufinamide.

The same reaction conditions as described above in relation to the first aspect of the invention may be applied to this step.

The 2-(azidomethyl)-1,3-difluorobenzene of formula III may have been prepared by reacting a 2,6-difluorobenzylhalide of formula II, wherein X is chloride, bromide, or iodide, with an azide to obtain the 2-(azidomethyl)-1,3-difluorobenzene of formula III.

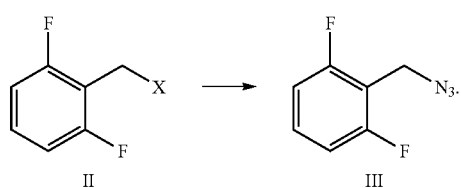

The same reaction conditions as described above in relation to the first aspect of the invention may be applied to this step.

DETAILED DESCRIPTION OF THE INVENTION

The invention will now be described in detail in connection with certain preferred and optional embodiments, so that various aspects thereof may be more fully understood and appreciated.

The process of the present invention involves the synthesis of rufinamide and may employ water as a solvent which contributes to green chemistry. The present invention describes a practical, economical and efficient synthesis for the preparation of rufinamide. This process is particularly advantageous in comparison with known methods because the reaction may be carried out without isolating the intermediates formed by the preceding step. The process of the present invention eliminates the risk of handling hazardous chemicals, the enhanced cost associated with multiple reactors, and it reduces the reaction time and cleanup, thus making the process more industrially viable.

In an embodiment of the present invention, there is provided an improved process for synthesis of rufinamide as depicted below in reaction Scheme 2,

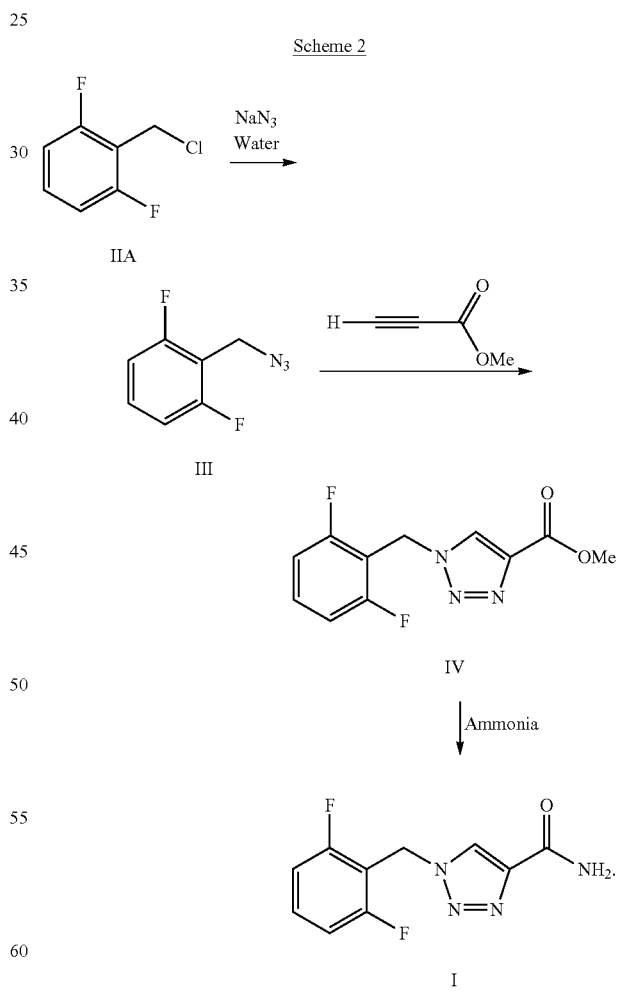

Scheme 2

Accordingly, in an embodiment, the present invention provides a process for the preparation of rufinamide of formula I, which process comprises: (a) reacting 2,6-difluorobenzylchloride of formula IIA

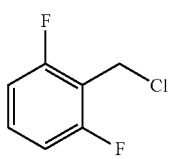

with sodium azide in the presence of water to obtain a 2-(azidomethyl)-1,3-difluorobenzene intermediate of formula III;

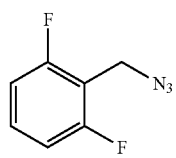

(b) reacting the intermediate of formula III with methyl propiolate in the presence of water as the solvent to obtain methyl 1-(2,6-difluorobenzyl)-1H-1,2,3-triazole-4-carboxylate of formula IV; and

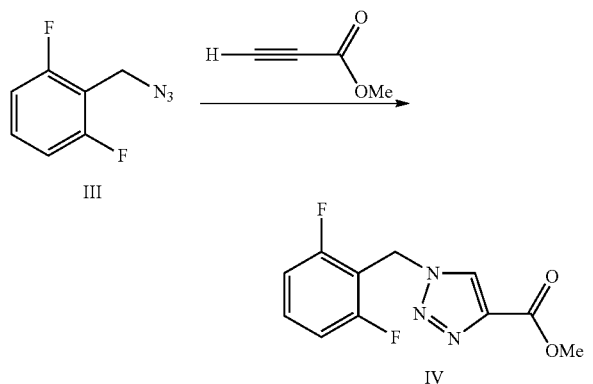

(c) reacting the intermediate of formula IV with ammonia to yield rufinamide of formula I.

In an embodiment, the process is carried out without isolation of 2-(azidomethyl)-1,3-difluorobenzene and without isolation of methyl 1-(2,6-difluorobenzyl)-1H-1,2,3-triazole-4-carboxylate. In another embodiment, the process is carried out as a one-pot process. Alternatively, the process may be carried out with isolation of the intermediates.

Step B—Preparation of methyl 1-(2,6-difluorobenzyl)-1H-1,2,3-triazole-4-carboxylate:

In an embodiment, water is the solvent in each of steps (i), (ii), and (iii). Water is advantageous over the environmentally-unfriendly organic solvents as used in the prior art. Further, the use of water reduces the production cost, simplifies the work-up, and minimizes the effluent disposal problem.

In an embodiment, step (a) is carried out at a temperature ranging from about 60° C. to about 80° C., preferably ranging from about 70° C. to about 75° C.

In an embodiment, the reaction time to produce the azide intermediate of formula III ranges from about 25 hours to about 40 hours, and preferably from about 25 hours to about 30 hours.

In another embodiment, in step (b), the 2-(azidomethyl)-1,3-difluorobenzene intermediate is subjected to a ring closure reaction by adding methyl propiolate dropwise at room temperature (about 25° C.) and then allowing the temperature to rise to a temperature ranging from about 50° C. to about 75° C., preferably to a temperature ranging from about 60° C. to about 65° C., and the time required for the reaction ranges from about 4 to about 5 hours.

In yet another embodiment, the amidation reaction of step (c) is carried out using ammonia which may be in the form of gaseous ammonia, liquid ammonia, or aqueous ammonia, preferably aqueous ammonia. Suitably, the concentration of the aqueous ammonia ranges from about 20% to about 25%. Typically, the aqueous ammonia is added dropwise. The reaction is preferably carried out at a temperature ranging from about 65° C. to about 80° C., more preferably from about 70° C. to about 75° C.

The reaction contents are cooled to room temperature (about 25° C.), washed with water and then dried under vacuum to obtain solid rufinamide.

In still another embodiment, rufinamide is prepared by isolating the intermediates obtained at each preceding step.

The invention also relates to the use of rufinamide preferably in the form of pharmaceutical preparations for the treatment of epilepsy and subindications thereof.

The following examples, which include preferred embodiments, will serve to illustrate the practice of this invention, it being understood that the particulars shown are by way of example and for purpose of illustrative discussion of preferred embodiments of the invention.

EXAMPLES

Example 1

One-pot Preparation of 1-[(2,6-Difluorophenyl)methyl]-1H-1,2,3-triazole-4-carboxamide (rufinamide):

In a 250 ml round bottom flask, 2,6-difluorobenzylbromide (0.024 mol, 5 g), sodium azide (0.026 mol, 1.72 g) and water (50 ml) were added. The reaction mixture was heated to 70° C. to 75° C. for 30 hours and formation of the azide intermediate was monitored by thin layer chromatography (TLC). After the completion of reaction, the reaction contents were cooled to room temperature and then to this methyl propiolate (0.024 mol, 2.1 ml) was added dropwise, maintaining the contents at room temperature. On complete addition, the mixture was again heated at 60° C. to 65° C. for 4 to 5 hours. After the reaction was completed, the contents were cooled to room temperature and to this 25% aqueous ammonia (40 ml) solution was added dropwise. The reaction contents were heated to 70° C. to 75° C. for 4 to 5 hours and then gradually cooled to room temperature. The solid obtained was filtered and washed with water. The product was dried under vacuum at 70° C.-75° C. to give 3.0 g of rufinamide.

Example 2

Multistep Preparation of 1-[(2,6-Difluorophenyl)methyl]-1H-1,2,3-triazole-4-carboxamide (rufinamide):
Step A—Preparation of 2-(azidomethyl)-1,3-difluorobenzene:

To a 250 ml round bottom flask, 2,6-difluorobenzylbromide (0.024 mol, 5 g), sodium azide (0.026 mol, 1.72 g) and water (50 ml) were charged. The reaction mixture was heated to 70° C. to 75° C. for 30 hours and formation of azide intermediate (99.4%) was monitored by gas chromatography. After completion of the reaction, the contents were cooled to room temperature. The layers of the reaction mixture were separated to obtain an upper water layer and a lower azide intermediate layer. The lower layer was then concentrated and dried under vacuum to obtain 3.8 g of the product.

Step B—Preparation of methyl 1-(2,6-difluorobenzyl)-1H-1,2,3-triazole-4-carboxylic Acid:

In a 250 ml round bottom flask, 2-(azidomethyl)-1,3-difluorobenzene (0.0207 mol, 3.0 g) as obtained from step A and water (50 ml) were charged. To this mixture methyl propiolate (0.0207 mol, 2.1 ml) was added dropwise at room temperature and then heated to 60° C. to 65° C. for 4 to 5 hours. The progress of the reaction was monitored by TLC. After the completion of reaction, the reaction mixture was cooled to room temperature. The solid obtained was filtered and then washed with water (10 ml). The product was dried under vacuum at 50° C. to 55° C. to give 2.5 g of methyl 1-(2,6-difluorobenzyl)-1H-1,2,3-triazole-4-carboxylate.

A mixture of intermediate obtained from step B (0.0098 mol, 2.5 g), and 20% aqueous ammonia solution (0.196 mol, 15 ml) was added to a 250 ml round bottom flask. The mixture was then stirred at 70° C. to 75° C. for 5 to 6 hours. After the completion of reaction, as monitored by TLC, the reaction mixture was cooled to room temperature. The solid obtained was filtered, washed with water and dried under vacuum at 60° C. to 65° C. to give a solid product (1.7 g).

It will be appreciated that the invention may be modified within the scope of the appended claims.

The invention claimed is:

1. A process for the preparation of rufinamide of formula I,

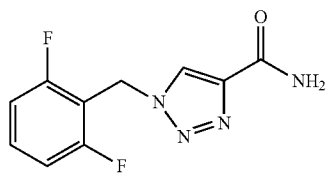

which process comprises: (i) reacting a 2,6-difluorobenzylhalide of formula II, wherein X is chloride, bromide or iodide, with an azide to obtain 2-(azidomethyl)-1,3-difluorobenzene of formula III;

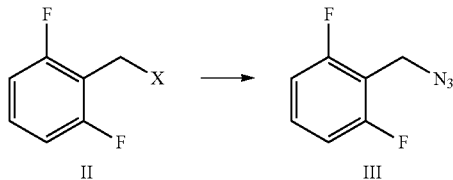

(ii) reacting 2-(azidomethyl)-1,3-difluorobenzene of formula III with methyl propiolate to obtain methyl 1-(2,6-difluorobenzyl)-1H-1,2,3-triazole-4-carboxylate of formula IV; and

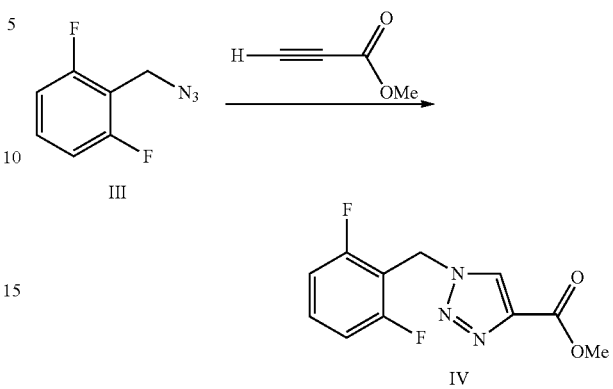

(iii) reacting methyl 1-(2,6-difluorobenzyl)-1H-1,2,3-triazole-4-carboxylate of formula IV with ammonia to obtain rufinamide of formula I.

2. The process according to claim 1, wherein X is chloride.

3. The process according to claim 1, wherein X is bromide.

4. The process according to claim 1, wherein the azide is an alkali metal azide.

5. The process according to claim 4, wherein the alkali metal azide is sodium azide or potassium azide.

6. The process according to claim 4, wherein the alkali metal azide is sodium azide.

7. The process according to claim 1, wherein the azide is trimethylsilyl azide.

8. The process according to claim 1, wherein the azide is diphenylphosphoryl azide.

9. The process according to claim 1, wherein the ammonia in step (iii) is in the form of aqueous ammonia.

10. The process according to claim 1, wherein all the reaction steps are carried out in the presence of water as a solvent.

11. The process according to claim 1, wherein steps (i) to (iii) are carried out without isolation of 2-(azidomethyl)-1,3-difluorobenzene of formula III and without isolation of methyl 1-(2,6-difluorobenzyl)-1H-1,2,3-triazole-4-carboxylate of formula IV.

12. The process according to claim 1, wherein the process is a one-pot process.

* * * * *